United States Patent [19]

Levin et al.

[11] Patent Number: 5,284,853
[45] Date of Patent: Feb. 8, 1994

[54] ANGIOTENSIN II RECEPTOR BLOCKING 2,3,6 SUBSTITUTED QUINAZOLINONES

[75] Inventors: Jeremy I. Levin, Nanuet; Aranapakam M. Venkatesan, Elmhurst, both of N.Y.

[73] Assignee: American Cyanamid Company, Wayne, N.J.

[21] Appl. No.: 52,943

[22] Filed: Apr. 23, 1993

[51] Int. Cl.$^5$ ................ A61K 31/505; C07D 413/10; C07D 413/14
[52] U.S. Cl. .................... 514/259; 544/90; 544/229; 544/284; 544/287; 546/338; 549/75; 549/491; 549/492; 558/299
[58] Field of Search ............... 544/284, 287; 514/259

[56] References Cited

U.S. PATENT DOCUMENTS

| | | | |
|---|---|---|---|
| 5,162,325 | 11/1992 | Chakravarty et al. | 514/259 |
| 5,202,322 | 4/1993 | Allen | 514/228.2 |
| 5,204,354 | 4/1993 | Chakravarty et al. | 544/284 |
| 5,240,928 | 8/1993 | Allen et al. | 514/259 |

FOREIGN PATENT DOCUMENTS

| | | |
|---|---|---|
| 407342 | 1/1991 | European Pat. Off. |
| 411766 | 2/1991 | European Pat. Off. |
| 445811 | 9/1991 | European Pat. Off. |
| 481448 | 4/1992 | European Pat. Off. |
| 512870 | 11/1992 | European Pat. Off. |

*Primary Examiner*—Emily Bernhardt
*Attorney, Agent, or Firm*—Thomas S. Szatkowski

[57] ABSTRACT

The invention provides novel 2, 3, 6 substituted quinazolinones of the formula

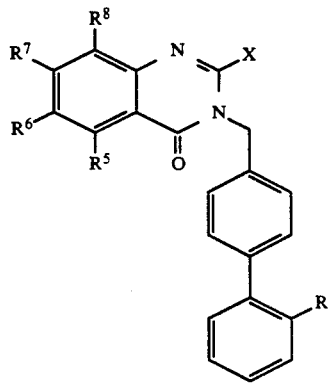

Formula I wherein, R, $R^6$ and X are defined in the specification which have activity as angiotensin II (AII) antagonists.

21 Claims, No Drawings

ANGIOTENSIN II RECEPTOR BLOCKING 2,3,6 SUBSTITUTED QUINAZOLINONES

BACKGROUND OF THE INVENTION

Field of the Invention

This invention relates to certain novel 2, 3, substituted quinazolinone compounds which have demonstrated activity as angiotensin II (AII) antagonists and are therefore useful in alleviating angiotensin induced hypertension and for treating congestive heart

SUMMARY OF THE INVENTION

According to the present invention, there are provided novel compounds of Formula I which have angiotensin II-antagonizing properties and are useful as antihypertensives:

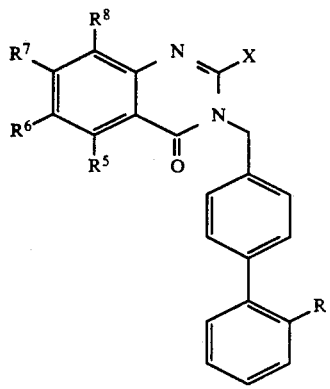

Formula I wherein:
R is

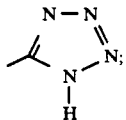

X is straight or branched alkyl of 3 to 5 carbon atoms;
$R^6$ is

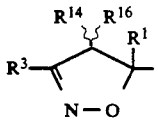

$R^1$ is H, straight chain lower alkyl of 1 to 4 carbon atoms, —CP_3, —CN,

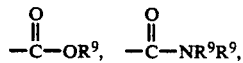

phenyl, substituted phenyl (substitution selected from monolower alkyl of 1 to 3 carbon atoms, —CF_3, nitro, O-alkyl of 1 to 3 carbon atoms), pyridine, thiophene or furan;
$R^3$ is —CO_2R^9,

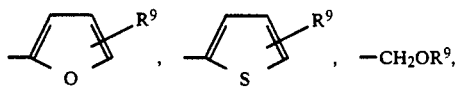

phenyl, substituted phenyl (substitution selected from mono-lower alkyl of 1 to 3 carbon atoms, —CF_3, nitro, O-alkyl of 1 to 3 carbon atoms), pyridine, —CN, alkyl (C_1-C_6, straight or branched),

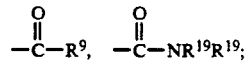

$R^{14}$ and $R^{16}$ are hydrogen, straight or branched chain lower alkyl of 1 to 4 carbon atoms, —CO_2R^9, —CN, phenyl, substituted phenyl (substitution selected from mono-lower alkyl of 1 to 3 carbon atoms, —CF_3, nitro, O-alkyl of 1 to 3 carbon atoms), pyridine, thiophene or furan,

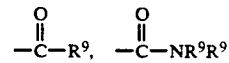

$R^{19}$ is straight or branched chain lower alkyl of 1 to 4 carbon atoms;
$R^9$ is hydrogen, straight or branched chain lower alkyl of 1 to 4 carbon atoms; and pharmaceutically acceptable salts of these compounds.

The present invention also provides novel intermediate compounds, methods for making the novel 2, 3, 6 substituted quinazolinone angiotensin II antagonizing compounds, methods for making the novel intermediates, methods of using the novel quinazolinone angiotensin II antagonizing compounds to treat hypertension, congestive heart failure and to antagonize the effects of angiotensin II.

DETAILED DESCRIPTION OF THE INVENTION

The novel compounds of the present invention are prepared according to the following reaction schemes.

Referring to Scheme I, the corresponding anthranilic acid 2 wherein $R^{10}$ is I, Br or CH_3, is heated to reflux in alkyl acid anhydride 3 wherein X is alkyl of 3 to 5 carbon atoms to provide the 4H-3,1-benzoxain-4-ones 4 which are isolated by concentrating the reaction mixtures and used without further purification. When the 4H-3,1-benzoxazin-4-ones 4 are refluxed in ethyl alcohol containing ammonia, or ammonium hydroxide solution, the quinazolinone intermediates 5 are obtained.

Scheme I

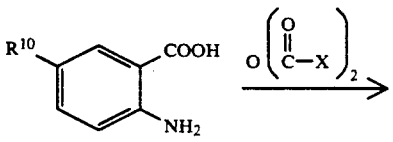

-continued
Scheme I dichromate in N,N-dimethylformamide to afford ketone 11.

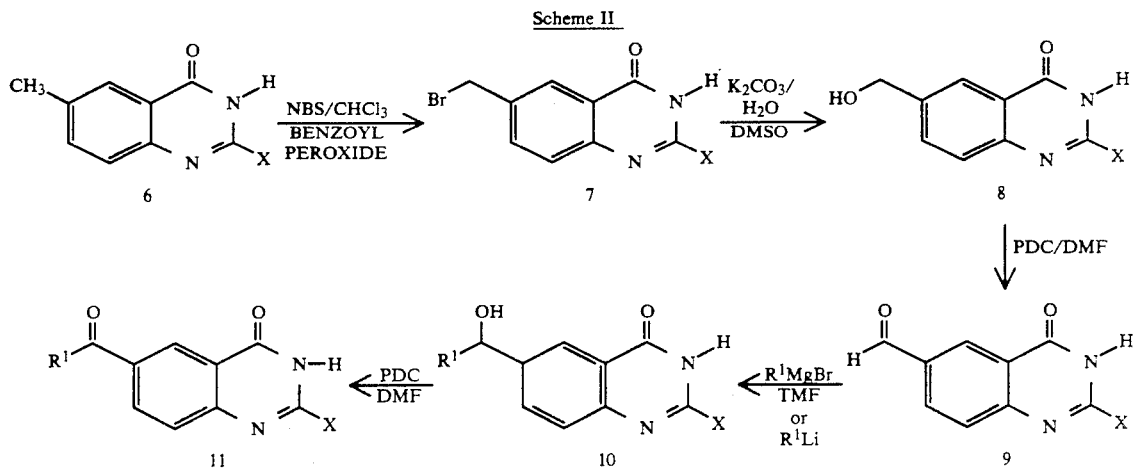

Scheme II

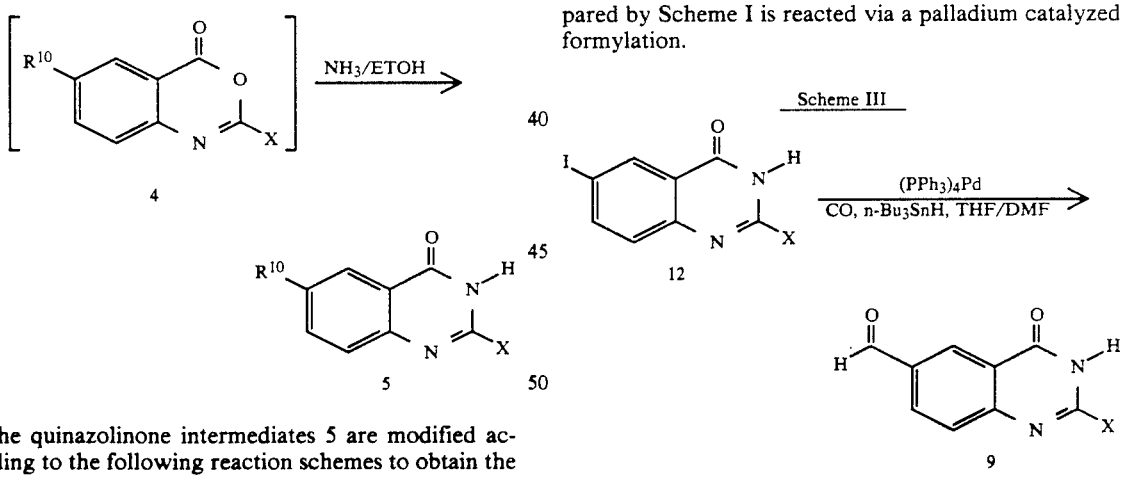

The quinazolinone intermediates 5 are modified according to the following reaction schemes to obtain the novel quinazolinone angiotensin II antagonizing compounds of the present invention.

In Scheme II, 6-methylquinazolinone 6, as prepared by Scheme I, is brominated with N-bromosuccinimide to give the bromomethyl compound 7. Hydrolysis of the bromide with aqueous potassium carbonate in dimethylsulfoxide yields the primary alcohol 8. The alcohol 8 is oxidized with pyridinium dichromate in N,N-dimethylformamide to afford aldehyde 9. The aldehyde 9 is reacted with a variety of Grignard Reagents $R^1MgBr$ or lithium reagents $R^1$ Li in tetrahydrofuran where $R^1$ is hereinbefore defined, with the proviso that for this reaction scheme $R^1$ cannot be H, $-CF_3$, $-CN$, $-CO_2R^9$, $-CONR^9R^9$ to give the desired secondary alcohol 10. Alcohol 10 is oxidized with pyridinium dichromate in N,N-dimethylformamide to afford ketone 11.

In an alternate route to 9, as shown in Scheme III, 2-alkylsubstituted-6-iodo-4(1H)-quinazolinone 12, prepared by Scheme I is reacted via a palladium catalyzed formylation.

As shown in Scheme IV, the palladium (II) catalyzed coupling of (trimethylsilyl)acetylene with 2-alkylsubstituted-6-iodo-4(1H)-quinazolinone 12 yields the acetylenic quinazolinone 13. Desilylation of the acetylene with sodium hydroxide in water-methanol gives the terminal acetylene 14. Hydration of acetylene 14 with catalytic mercuric sulfate-sulfuric acid in acetic acid affords methyl ketone 15. The palladium (II) catalyzed coupling of substituted acetylenes where $R^{17}$ is defined as straight or branched lower alkyl of 1 to 30,.It 4 carbon atoms with 2-alkylsubstituted-6-iodo-4(1H)-quinazolinone 12 yields the acetylenic quinazolinone 16. Hydration of 1-6 with catalytic mercuric sulfate-sulfuric acid in acetic acid gives ketone 17.

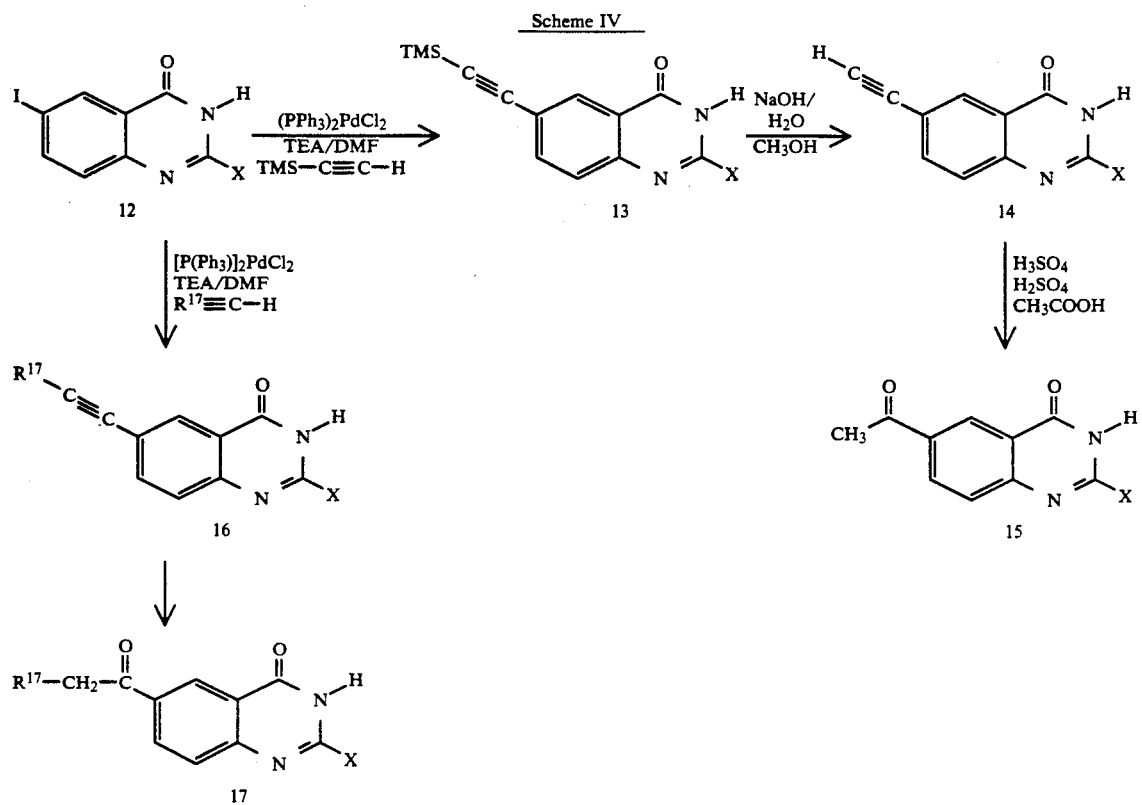

In addition as shown in Scheme V, acetylene 14 is hydrogenated over 5% palladium-barium sulfate in pyridine to give either the terminal olefin 18 or the ethyl substituted quinazolinone 19. Also, acetylene 16 is hydrogenated over 5% palladium-barium sulfate in pyridine to give olefin 20 and alkyl substituted quinazolinone 21.

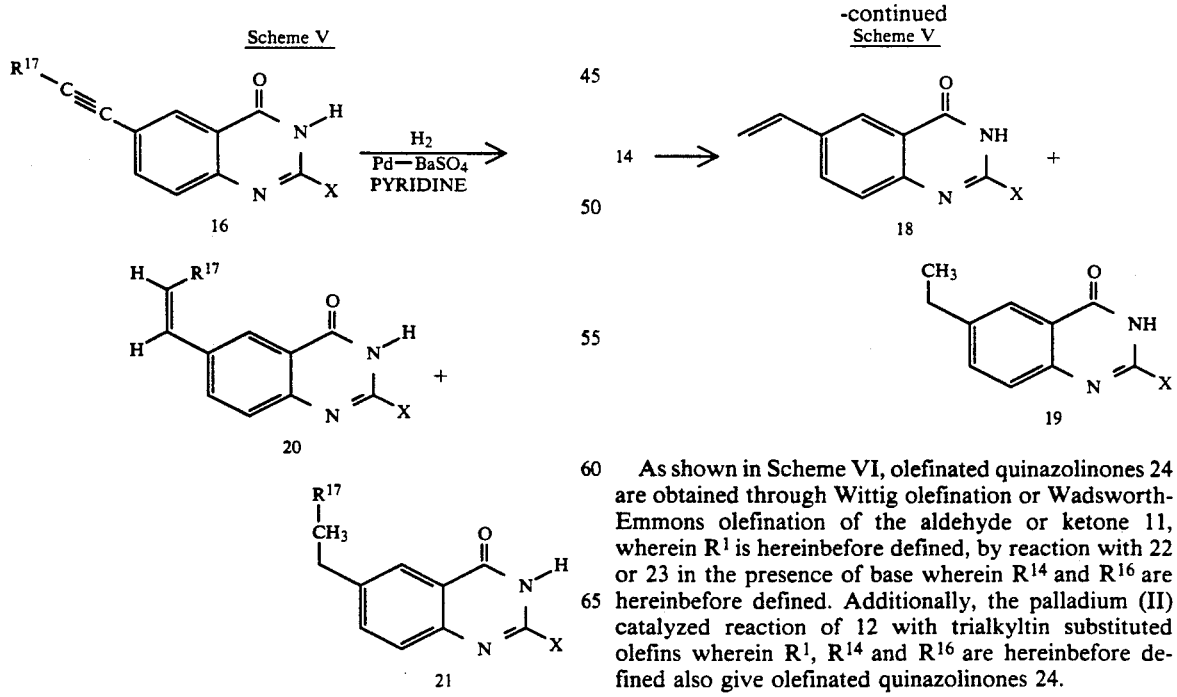

As shown in Scheme VI, olefinated quinazolinones 24 are obtained through Wittig olefination or Wadsworth-Emmons olefination of the aldehyde or ketone 11, wherein $R^1$ is hereinbefore defined, by reaction with 22 or 23 in the presence of base wherein $R^{14}$ and $R^{16}$ are hereinbefore defined. Additionally, the palladium (II) catalyzed reaction of 12 with trialkyltin substituted olefins wherein $R^1$, $R^{14}$ and $R^{16}$ are hereinbefore defined also give olefinated quinazolinones 24.

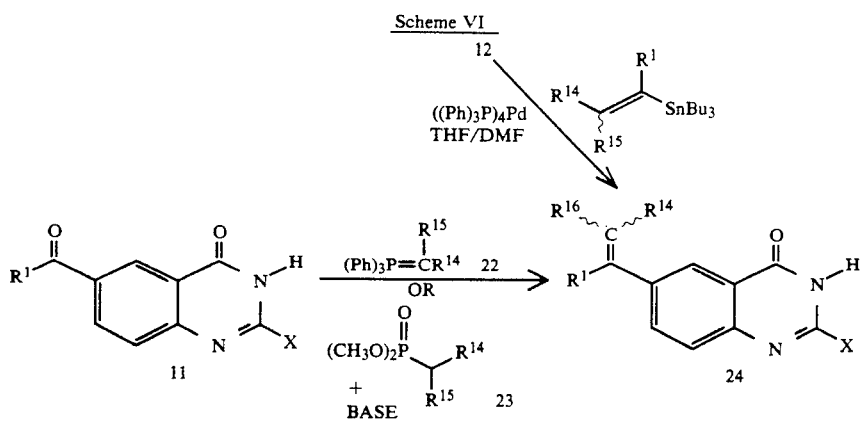

As described in EP 0,497,150, biphenyl 25 is attached to quinazolinone intermediate 12 by initially alkylating the quinazolinone with a para-substituted benzyl bromide and subsequently attaching a second phenyl moiety containing a trityl protected tetrazole or a cyano via a transition metal catalyzed coupling at the para position of the first phenyl ring.

Alternatively, the coupling of quinazolinone intermediate 12 where X is hereinbefore defined with biphenyl 25 where $R^{18}$ is a trityl protected tetrazole prepared by the methods of N. B. Mantlo, J. Med. Chem. 34, 2919-2922 (1991) or cyano prepared by the methods outlined in D. J. Carini, J. Med. Chem. 34, 2525-2547 (1991) is illustrated in Scheme VII and gives coupled product 26 by dissolving 12 and 25 in acetone or another suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA) or lithium hexamethyldisilazide for 2-48 hours, at 20-60° C. The obtained alkylated quinazolinone 26 may be purified by chromatography or used as is in further transformations and/or deprotection.

Scheme VII

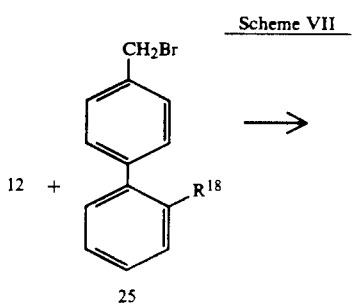

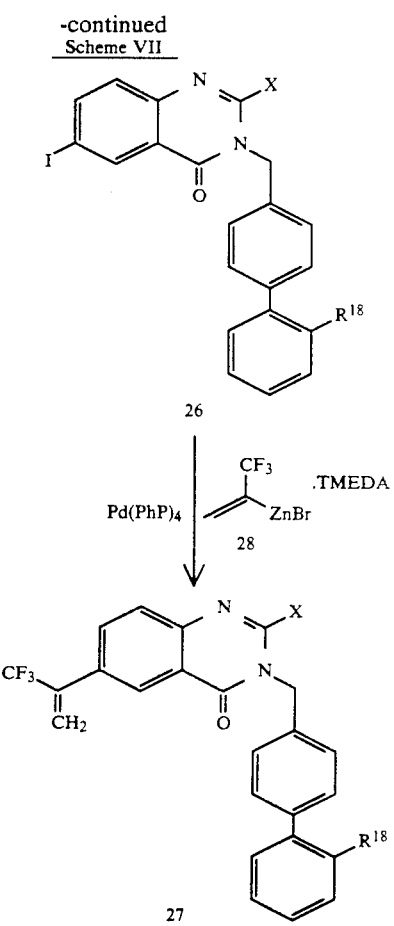

Alkylated quinazolinone 26 is converted to the trifluoromethyl olefin 27 through palladium catalyzed coupling with trifluoroisopropenylzinc reagent 28 (Jiang, B.; Xu, Y.; J. Org. Chem. 56, 7336 (1991)).

The coupling of cluinazolinone 15 where X is hereinbefore defined with biphenyl 25 where $R^{18}$ is hereinbefore defined, using the coupling method shown in Scheme VII, is illustrated in Scheme VIII to give alkylated quinazolinone 29. Reaction of alkylated quinazolinone 29 with trimethylsilyl cyanide in the presence of zinc iodide (Oda, M.; Yamamuro, A.; Watabe, T., Chem. Lett, 1427 (1979)) gives the trimethylsilylcyanohydrin 30 where $R^{18}$ is the free tetrazole which is further reacted with phosphorous oxychloride in pyridine to give the cyano substituted olefin 31.

Scheme VIII

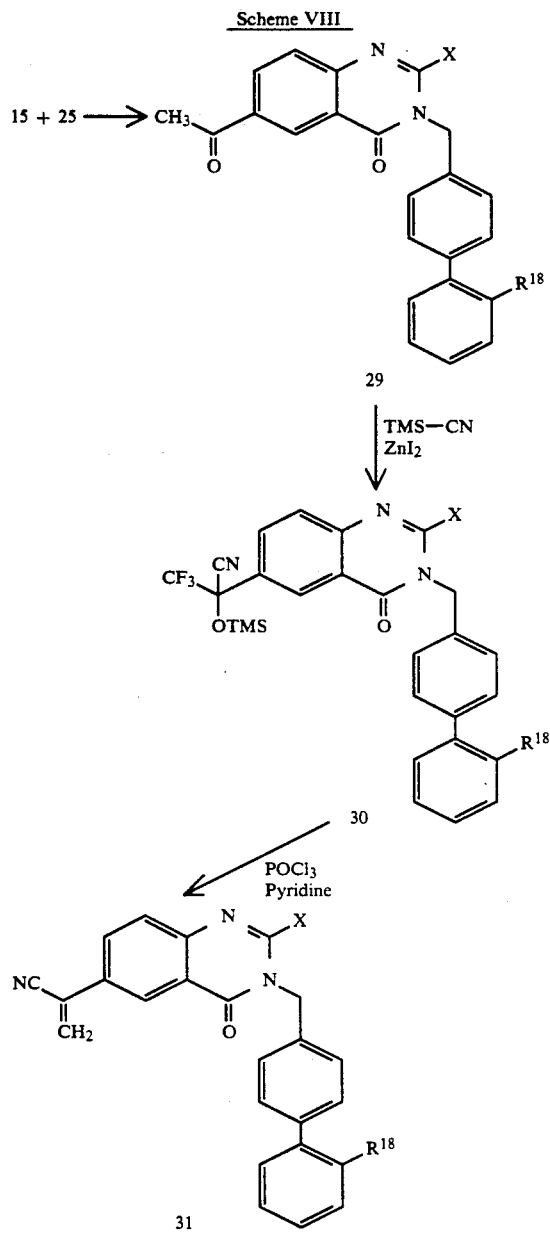

Alternatively, as shown in Scheme IX, 1,1-disubstituted olefins are prepared by the addition of a Grignard reagent $R^1MgBr$, to 29 where $R^1$ is hereinbefore defined, with the proviso that for this reaction scheme $R^1$ cannot equal H, —$CF_3$, —CN, —$CO_2R^9$, —$CONR^9R^9$ to provide alcohol 32. The alcohols are dehydrated with (bis-{α,α-bis(trifluoromethyl)benzenemethanolato}-diphenylsulfur} or with sulfuric, hydrochloric, or p-toluenesulfonic acid to give the desired alkenes 33.

Scheme IX

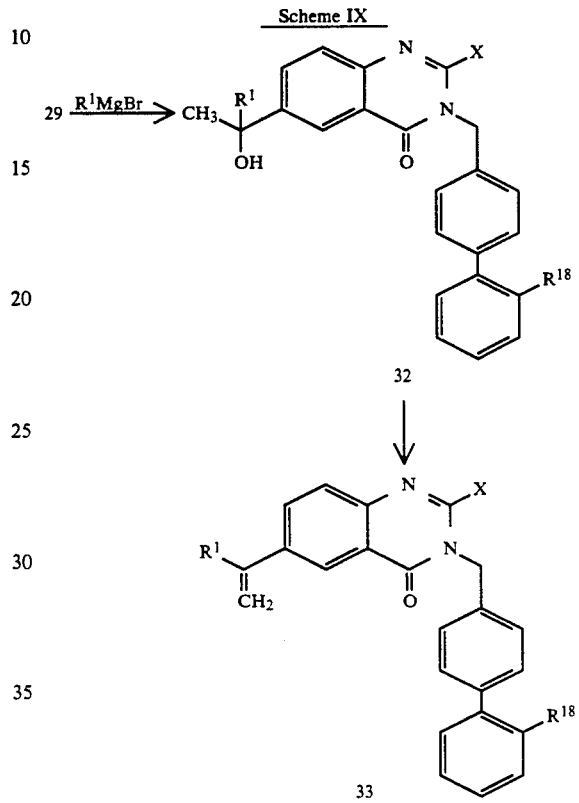

The synthesis of α,β-unsaturated esters and amides is illustrated in Scheme X. Quinazolinone 29 is reacted with enol triflates (Scott, W. J., McKurry, J. E., Accounts of Chemical Research 21(2), 47(1988)) to afford 34. Palladium catalyzed coupling of 34 (Cacchi, S.; Morera, E.; Ortar, G., Tet. Letters, 26(8), 1109(1985)) gives either the ester 35 when alcohol $R^9OH$, where $R^9$ is hereinbefore defined, is used or amide 36 when the amine $H-N(R^9)_2$, where $R^9$ is hereinbefore defined, is used.

Scheme X

Scheme X
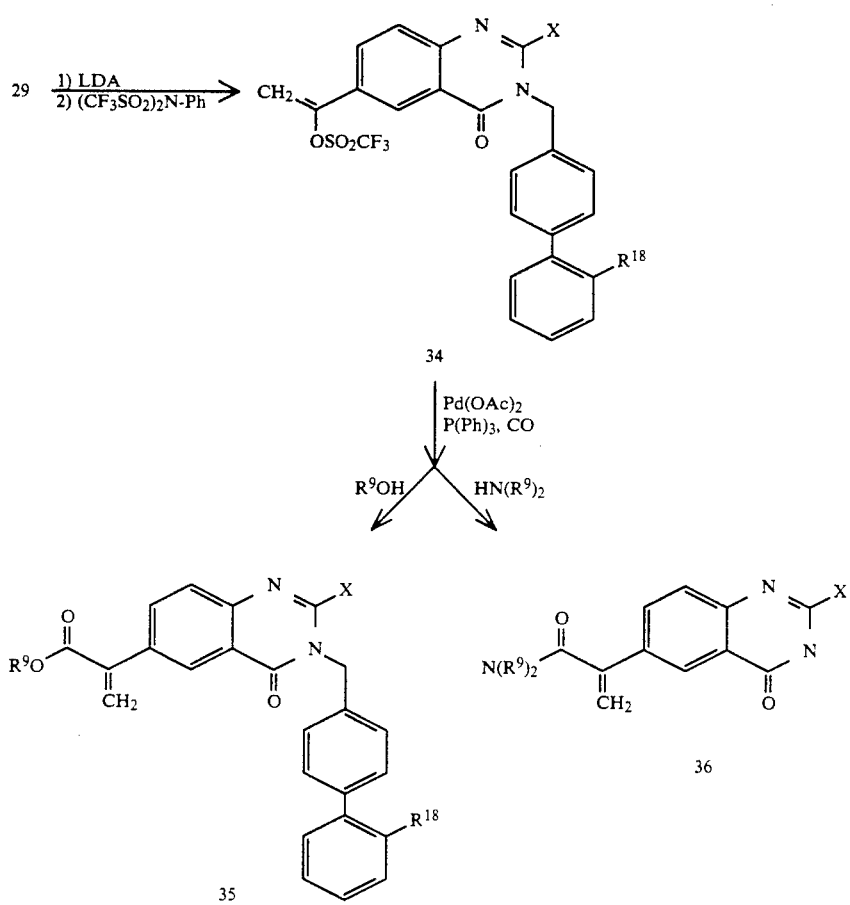
Scheme XI
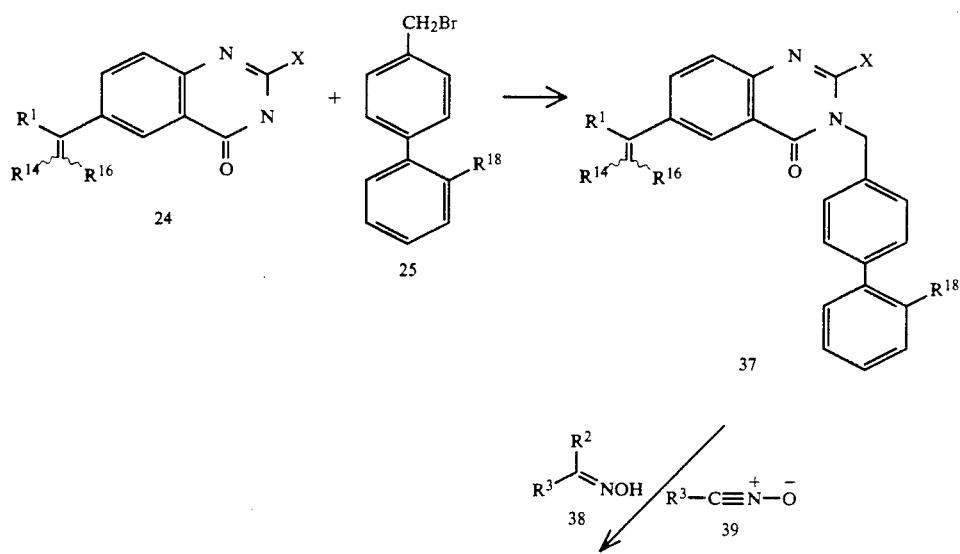

Scheme XI -continued

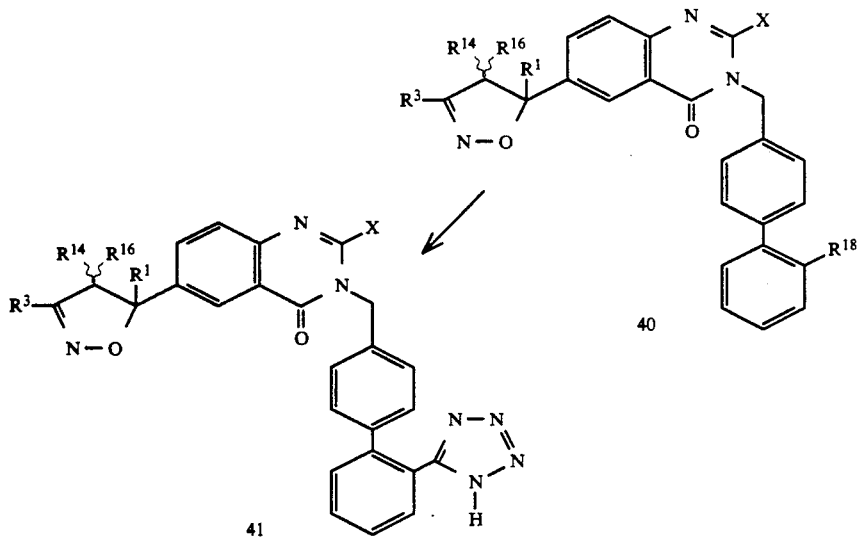

As described in EP 0,497,150, biphenyl 25 is attached to quinazolinone intermediate 24 by initially alkylating the quinazolinone with a para-substituted benzyl bromide and subsequently attaching a second phenyl moiety containing a trityl protected tetrazole or a cyano via a transition metal catalyzed coupling at the para position of the first phenyl ring. Alternatively, as shown in Scheme XI, quinazolinone 24 where $R^1$, $R^{14}$, $R^{16}$ and X are hereinbefore defined and the biphenyl 25 where $R^{18}$ is a tritylprotected tetrazole prepared by the methods of N. B. Mantlo, J. Med. Chem. 34, 2919-2922 (1991) or cyano prepared by methods outlined in D. J. Carini, J. Med. Chem. 34, 2525-2547 (1991) are dissolved in acetone or another suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, sodium t-butoxide, lithium methoxide, potassium t-butoxide, lithium diisopropylamide (LDA) or lithium hexamethyl disilazide for 2-48 hours, at 20-60° C. The obtained alkylated quinazolinones 37 may be purified by chromatography or used as is in further transformations and/or deprotection.

Reaction of 37 with oxime 38 where $R^3$ is hereinbefore defined and $R^2$ is H in the presence of N-chlorosuccinimide, triethylamine and pyridine in chloroform at room temperature wherein $R^1$, $R^3$, $R^{14}$, $R^{16}$ and X are hereinbefore defined or with oxime 38 where $R^3$ is hereinbefore defined and $R^2$ is Cl in the presence of triethylamine and pyridine or with nitrile oxide 39 affords substituted quinazolinone 40. Reaction of 40 where $R^{18}$ is cyano with sodium azide in the presence of tri-n-butyltin chloride in refluxing xylene affords the desired tetrazole 41. Contemplated equivalents to tri-n-butyltin chloride include tri-(loweralkyl $C_1$-$C_4$) tin chlorides and bromides. Contemplated equivalents to sodium azide include lithium azide. Hydrolysis of 40 where $R^{18}$ is a trityl protected tetrazole with methanol-tetrahydrofuran at room temperature to reflux or a catalytic amount of hydrochloric acid or other suitable acid such as sulfuric, trifluoroacetic or hydrogen chloride for 10 minutes to 24 hours at room temperature affords the free tetrazole 41.

Scheme XII

As shown in Scheme XII, the nitrile oxide 39 can be generated from nitro compound 40 where $R^3$ is hereinbefore defined by reaction with p-chlorophenylisocyanate in the presence of triethylamine using the conditions of Mukaiyama, T., Hoshino, T., J. IW. Chem. Soc. 5339 (1960).

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in Remington's Pharmaceutical Sciences, 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium, magnesium and ammonium salts.

Some of the compounds of the hereinbefore described schemes have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionitrile or any other protecting group suitable for protecting the tetrazole nitrogen. Additionally, it will be apparent to those skilled in the art that removal of the various nitrogen protecting groups, other than trityl, may require methods other than dilute acid.

The compounds of this invention and their preparation are illustrated by the following non-limiting examples.

EXAMPLE 1

2-Butyl-6-(methyl)-4(1H)-quinazolinone

To 20.0 g of 2-amino-5-methylbenzoic acid is added 60 ml of valeric anhydride. The mixture is heated at reflux for 18 hours and then concentrated under reduced pressure. The resulting brown solid residue is dissolved in a mixture of 200 ml of 30% of ammonium hydroxide solution and 300 ml of ethyl alcohol. This mixture is heated at reflux for 5 hours and then allowed to cool to room temperature. After cooling, the precipitate is collected by filtration. The cake is washed with ethanol and water, then dried under vacuum to give 8.92 g of the quinazolinone as a white solid. CI MASS SPEC MH+ =217.

EXAMPLE 2

2-Butyl-6-iodo-4(1H)-quinazolinone

The method of Example 1 is used with 2-amino-5-iodobenzoic acid to prepare the desired product, M.P. 257-258° C.

EXAMPLE 3

2-Butyl-6-(bromomethyl)-4(1H)-quinazolinone

To a suspension of 3.50 g of 6-methylquinazolone in 100 ml of chloroform is added 3.39 g of N-bromosuccinimide and 0.25 g of benzoyl peroxide. The reaction mixture is heated at reflux for 18 hours and then filtered hot. A precipitate of 2.21 g of an inseparable mixture of the desired bromide and starting 6-methyl-quinazolinone is obtained and used in Example 4 without further purification.

EXAMPLE 4

2-Butyl-6-(hydroxymethyl)-4(1H)-quinazolinone

To a suspension of 2.0 g of impure 2-butyl-6-(bromomethyl)-4(1H)-quinazolinone (Example 3) in 35 ml of dimethylsulfoxide and 20 ml of water is added 1.0 g of potassium carbonate. The reaction mixture is heated at reflux for 6 hours, resulting in a complete solution. Upon cooling slowly to room temperature a white precipitate forms and is collected by filtration. The filter cake is purified by flash chromatography on silica gel, eluting with 9:1 chloroform-reethanol to give 0.67 g of the desired product as a white solid. CI MASS SPEC 233(MH+).

EXAMPLE 5

2-Butyl-1,4-dihydro-4-oxo-6-cruinazolinecarboxaldehyde

To a solution of 0.3 g of 2-butyl-6-(hy-droxymethyl)-4(1H)-quinazolinone in 3.5 ml of dry N,N- dimethylformamide is added 1.7 g of pyridinium dichromate. The reaction mixture is stirred at room temperature for 16 hours and then poured into 125 ml of water. The resulting precipitate is removed by filtration and the filtrate extracted with 9:1 chloroform-methanol. The combined organic extracts are dried over magnesium sulfate, filtered and concentrated in vacuo and combined with the precipitate above. The combined solids are purified by flash chromatography on silica gel by eluting with 1:1 ethyl acetate-hexanes to give 0.27 g of the desired product. CI MASS SPEC 231(MH+).

EXAMPLE 6

2-Butyl-6-(l-hydroxyethyl)-4(1H)-quinazolinone

To a solution of 0.60 g of 2-butyl-1,4-dihydro-4-oxo-6-quinazolinecarboxaldehyde in 30 ml of dry tetrahydrofuran, cooled to-0° C. is added dropwise, 2.61 ml of a 3.0M solution of methylmagnesium bromide in diethyl ether. The reaction is stirred at 0° C. for 30 minutes and then quenched with 10 ml of aqueous ammonium chloride. After diluting with 10 ml of water, the reaction mixture is extracted with 9:1 chloroformmethanol. The combined extracts are dried with magnesium sulfate, filtered and concentrated to yield 0.64 g of the desired product. CI MASS SPEC 247(MH+).

EXAMPLE 7

2-Butyl-6-(l-hydroxypropyl)-4(1H)-quinazolinone

To a solution of 0.25 g of 2-butyl-1,4-dihydro-4-oxo-6-quinazolinecarboxaldehyde in 10 ml of dry tetrahydrofuran, cooled to 0° C., is added 1.63 ml of 2.0M ethyl magnesium bromide in tetrahydrofuran. The reaction mixture is stirred for 30 minutes at 0° C. and quenched with 20 ml of saturated ammonium chloride solution and 20 ml of water. The reaction mixture is extracted with 9:1 chloroform-methanol, dried over magnesium sulfate, filtered and evaporated in vacuo to give 0.26 g of the desired product. CI MASS SPEC 261(MH+).

EXAMPLE 8

2-Butyl-1,4-dihydro-4-oxo-6-cruinazolinecarboxaldehyde

To a solution of 1.0 g of 2-butyl-6-iodo-4(1H)-quinazolinone and 0.355 g of tetrakis(triphenylphosphine)palladium in 15 ml of tetrahydrofuran and 5 ml of N,N-dimethylformamide, heated to 55° C. under an atmosphere of carbon monoxide is added a solution of 1.40 g of tri-n-butyltin hydride in 2.5 ml of toluene over 6 hours via a syringe pump. After the addition is complete the reaction is allowed to cool to room temperature, diluted with brine and extracted with chloroform. The combined organics are concentrated in vacuo and the resulting residue triturated with ether. The precipitate is collected by filtration and purified by flash chromatography on silica gel, eluting with 1:1 ethyl acetate-hexanes to give 0.35 g of the desired product, m.p. 242-244° C.

EXAMPLE 9

2-Butyl-6-[(trimethylsilyl)ethylnyl]-4(1H)-quinazolinone

To a solution of 1.0 g of 2-butyl-6-iodo-4(1H)-quinazolinone 0.043 g of bis(triphenylphosphine) palladium (II) chloride and 5.8 mg of copper (I) iodide in 5.0 ml of N,N-dimethylformamide and 5.0 ml of triethylamine is added 0.36 g of (trimethylsilyl) acetylene. The resulting reaction mixture is heated at 45° C. for 1 hour and then 65° C. for 5 hours. Upon cooling, the reaction mixture is concentrated in vacuo and the residue purified by flash chromatography on silica gel, eluting with 1:3 ethyl acetate-hexane to yield 0.75 g of the desired product as a white solid. CI MASS SPEC 299(MH+).

EXAMPLE 10

2-Butyl-6-ethylnyl-4(1H)-quinazolinone

To a solution of 0.70 g of 2-butyl-6-[(trimethylsilyl)ethynyl]-4(1H)-quinazolinone in 20 ml of methanol and 20 ml of tetrahydrofuran is added 10.0 ml of 1.0 N sodium hydroxide solution. The reaction is stirred at room temperature for 2 hours and then diluted with 5% hydrochloric acid solution until the pH is 2. The resulting tan precipitate is collected by filtration and dried in vacuo to yield 0.50 g of the desired product. CI MASS SPEC 227(MH+).

EXAMPLE 11

6-Acetyl-2-butyl-4(1H)-quinazolinone

To A solution of 1.20 g of 2-butyl-6-ethynyl-4(1H)-quinazolinone in 90 ml of acetic acid is added 0.45 g of mercuric sulfate, 0.9 ml of water and 0.3 ml of sulfuric acid. The reaction mixture is heated at reflux for 5 hours, cooled to room temperature and quenched with 150 ml of water. The resulting mixture is concentrated in vacuo, diluted with 150 ml of water and extracted with 6:1 chloroform-reethanol. The combined organics are dried over magnesium sulfate, filtered and concentrated in vacuo. The residue is purified by flash chromatography on silica gel, eluting with 1:1 ethyl acetate-hexanes to give 0.67 g of the desired product as a white solid. CI MASS SPEC 245(MH+).

EXAMPLE 12

2-Butyl-6-(1-methylethenyl)-4(1H)-quinazolinone

To a suspension of 3.66 g of methyltriphenylphosphonium bromide in 30 ml of dry tetrahydrofuran, cooled to −78° C., is added dropwise 5.9 ml of a 1.73M solution of n-butyllithium in hexanes. Following complete addition, the reaction mixture is allowed to warm to room temperature and stirred for 15 minutes, until all the phosphonium bromide is dissolved. The reaction mixture is then recooled to −78° C. and a suspension of 6-acetyl-2-butyl-4(1H)-quinazolinone in 15 ml of dry tetrahydrofuran is added. The reaction is allowed to warm to room temperature and stirred for 24 hours followed by quenching with saturated ammonium chloride solution. After diluting with 10 ml of water, the aqueous layer is extracted with chloroform and the combined organics dried over magnesium sulfate, filtered and concentrated in vacuo. The residue is purified by flash chromatography on silica gel, eluting with 1:2 ethyl acetate-hexanes to give 0.23 g of the desired product as a white solid. CI MASS SPEC 243(MH

EXAMPLE 13

2-Butyl-6-(hydroxyphenylmethyl)-4(1H)-quinazolinone

To a stirred solution of 2.00 g of 2-butyl-1,4-dihydro-4-oxo-6-quinazolinecarboxaldehyde in 100 ml of tetrahydrofuran, cooled at 0° C., is added 13.0 ml of 2.0 M phenyllithium and stirring continued for 1 hour. The cooling is removed and the reaction allowed to reach room temperature followed by an additional 30 minutes at room temperature. The reaction is diluted with saturated ammonium chloride solution and extracted with ethyl acetate. The organic layer is dried, evaporated to a residue, which is purified by chromatography on silica gel by elution with 0.25:100 methanol-chloroform to give 0.932 g of the desired product. CI MASS SPEC 309(MH

EXAMPLE 14

2-Butyl-6-ethenyl-4(1H)-quinazolinone

A mixture of 2.00 g of 2-butyl-6-ethylnyl-4(1H)-quinazolinone and 0.200 g of 5% palladium-barium sulfate in 100 ml of pyridine is treated with 1 atmosphere of hydrogen at room temperature until 225 ml of hydrogen is used. The reaction mixture is filtered through diatomaceous earth and the cake washed with 100 ml of pyridine and 100 ml of methanol. The combined filtrates are evaporated to a residue which is purified by chromatography on silica gel using 1:2 ethyl acetate-hexanes to afford 0.786 g of the desired product. CI MASS SPEC 229 (MR+).

EXAMPLE 15

2-Butyl-6-ethenyl-4(1H)-cruinazolinone

A mixture of 12.28 g of 2-butyl-6-iodo-4(IH)-quinazolinone 0.866 g of tetrakis (triphenylphosphine)-palladium, 0.015 g of 2.,6-di-t-butyl-4-methylphenol in 75 ml of toluene and 20 ml of N,N-dimethylformamide is treated with 13.06 g of vinyltin followed by heating at reflux for 4 hours. The reaction mixture is evaporated in vacuo to a residue. The residue is diluted with hexanes and filtered. The cake is dissolved in 100 ml of 8:2 chloroformmethanol and filtered. The filtrate is absorbed on silica gel and the volatiles evaporated to a residue, which is chromatographed on silica gel using 1:3 ethyl acetate-hexanes to afford 4.55 g of the desired product. CI MASS SPEC 229 (MH+).

EXAMPLE 16

2-Butyl-6-ethenyl-3-[[2'-1-(triphenylmethyl)-1H-tetrazol-5-yl][1,1'-biphenyl]-4-yl]methyl-4(3H)-quinazolinone A suspension of 0.500 g of 2-butyl-6-ethenyl-4(1H)-quinazolinone, 1.44 g of 5-(4'-(bromomethyl)-[1,1'-biphenyl]-2-yl]-1-(triphenylmethyl)-1H-tetrazole and 0.908 g of anhydrous potassium carbonate in 60.0 ml of dry acetone is heated at reflux for 16 hours. The reaction mixture is allowed to cool to room temperature, filtered and the filtrate evaporated in vacuo. The residue is purified by chromatography on silica gel using 1:6 ethyl acetate-hexanes to afford 0.743 g of the desired product. FAB MASS SPEC 705 (M+H).

EXAMPLE 17

4'-[(2-Butyl-6-ethenyl-4-oxo-3(4H)-cruinazolinyl)-methyl][1,1'-biphenyl]-2-carbonitrile A mixture of 0.771 g of 2-butyl-6-ethenyl-4(lH)-quinazolinone, 1.104 g of 41-(bromomethyl)[1,1'-biphenyl]-2-carbonitrile, and 0.154 g of lithium methoxide in 15.0 ml of tetrahydrofuran is refluxed for 48 hours, cooled, concentrated in vacuo and the concentrate purified by chromatography on silica gel with 1:4 ethyl acetate-hexanes. Fractions containing the desired product are evaporated in vacuo, triturated with ether, filtered and dried to afford 0.974 g of the desired product. CI Mass Spec 420 (NH+)

EXAMPLE 18

4'-[[2-butyl-6-[4,5-dihydro-3-(5-methyl-2-furanyl)-5-isoxazolyl]-4-oxo-3(4H)-cruinazolinylimethyl][1,1'-biphenyll-2-carbonitrile A suspension of 0.080 g of N-chlorosuccinimide in 1.5 ml of chloroform and 3.4 μl of pyridine is stirred at room temperature while 0.075 g of 5-methyl-2-furan-2-carboxaldehyde oxime is added in one portion. The reaction mixture is stirred at room temperature for 0.5 hour. While stirring, 0.250 g of 4'-[(2-butyl-6-ethenyl-4-oxo-3(4H)-quinazolinyl)-methyl]-1,1'-biphenyl]-2-carbonitrile is added in one portion. Over 30 minutes 87 μl of triethylamine is added dropwise followed by stirring the reaction mixture overnight at room temperature. The reaction mixture is purified by chromatography on silica gel using 1:3 ethyl acetate-hexanes to afford 0.249 g of the desired product. FAB MASS SPEC 543 (M+H).

EXAMPLE 19

2-Butyl-6-r4,5-dihydro-3-(5-mothyl-2-furanyl)-5-isoxazolyl]-3-[[2'-(lH-tetrazol-5-yl)[1,1'-biphenyl]-4-yllmethyll-4(3H)-cruinazolinone A mixture of 0.228 g of 4'-[[2-butyl-6-[4,5-dihydro-3-(5-methyl-2-furanyl)-5-isoxazolyl]-4-oxo-3(4H)-quinazolinyl]methyl][1,1'-biphenyl]-2-carbonitrile, 0.082 g of sodium azide and 0.411 g of tri-n-butyltin chloride in 5.0 ml of xylene is refluxed for 48 hours. The cooled reaction mixture is diluted with 10 ml of 1.0 N sodium hydroxide and 10 ml of ether. The aqueous layer is separated, acidified with 10% HCl and extracted with chloroform. The organic layer is dried with $MgSO_4$, filtered and the filtrate purified by chromatography on silica gel using 9:1 chloroform-methanol to afford 0.226 g of the desired product. FAB MASS SPEC 586 (M+H),

EXAMPLE 20

4'-[[2-butyl-6-[4,5-dihydro-3-(5-methyl-2-thienyl)-5-isoxazolyl]-4-oxo-3(4H)-cruinazolinyllmethyl][1,1'-biphenyll-2-carbonitrile A suspension of 0.080 g of N-chlorosuccinimide in 1.5 ml of chloroform and 3.4 Al of pyridine is stirred at room temperature while 0.084 g of 5-methyl-2-thiophene-2-carboxaldehyde oxime is added in one portion. The reaction mixture is stirred at room temperature for 0.5 hour. While stirring, 0.250 g of 4'-[(2-butyl-6-ethenyl-4-oxo-3(4H)-quinazolinyl)methyl-][1,1'-biphenyl]-2-carbonitrile is added in one portion. Over 30 minutes 87 μl of triethylamine is added dropwise followed by stirring the reaction mixture overnight at room temperature. The reaction mixture is purified by chromatography on silica gel using 1:3 ethyl acetate-hexanes to afford 0.328 g of the desired product. FAB MASS SPEC 559 (M+H).

EXAMPLE 21

2-Butyl-6-[4,5-dihydro-3-(5-methyl-2-thienyl)-5-isoxazolyl]-3-[[2'-(lH-tetrazol-5-yl)[1,1'-biphenyl]-4-yllmethyll-4(3H)-cruinazolinone A mixture of 0.296 g of 41-[[2-butyl-6-[4,5-dihydro-3-(5-methyl-2-thienyl)-5-isoxazolyl]-4-oxo-3(4H)-quinazolinyl]methyl][1,11-biphenyl]-2-carbonitrile, 0.103 g of sodium azide and 0.518 g of tri-n-butyltin chloride in 5.0 ml of xylene is refluxed for 48 hours. The cooled reaction mixture is diluted with 10 ml of 1.0 N sodium hydroxide and 10 ml of ether. The aqueous layer is separated, acidified with 10% HCl and extracted with chloroform. The organic layer is dried with $MgSO_4$, filtered and purified by chromatography on silica gel using 9:1 chloroform-reethanol to afford 0.255 g of the desired product. FAB MASS SPEC 602 (M+H).

EXAMPLE 22

2-Butyl-6-[4,5-dihydro-3-(4-methylphenyl)-5-isoxazolyl]-3-[[2'-[1-(trinhenylmethyl)-lH-tetrazol-5-yl][1,1'-biphenyl-4-yl]methyl]-4(3H)-guinazolinone A suspension of 0.047 g of N-chlorosuccinimide in 1.0 ml of chloroform and 2.0 μl of pyridine is stirred at room temperature while 0.048 g of 4-methylbenzaldehyde oxime is added in one portion. The reaction mixture is stirred at room temperature for 0.5 hour. While stirring, 0.250 g of 2-butyl-6-ethenyl-3-[[2'-[1-(triphenylmethyl)-lH-tetrazol-5-yl][1,1'-bi-phenyl]-4-yl]methyl]-4(3H)-quinazolinone is added in one portion over 30 minutes, 52 μl of triethylamine is added dropwise followed by stirring the reaction mixture overnight at room temperature. The reaction mixture is purified by chromatography on silica gel using 1:3 ethyl acetate-hexanes to afford 0.183 g of the desired product. FAB MASS SPEC 860 (M+Na).

EXAMPLE 23

2-Butyl-6-[4,5-dihydro-3-(4-methylphenyl)-5-isoxazolyl]-3-[[2'-(lH-tetrazol-5-yl)[1,1'-biphenyl]-4-yl]methyl]-4(3H)-quinazolinone A mixture of 0.178 g of 2-butyl-6-[4,5-dihydro-3-(4-methylphenyl)-5-isoxazolyl]-3-[[2'-[1-(triphenylmethyl)-lH-tetrazol-5-yl][1,11-biphenyl-4-yl]methyl]-4(3H)-quinazolinone in 3.0 ml of tetrahydrofuran and 1.0 ml of water is refluxed for 18 hours. One drop of 5% HCl is added and reflux continued for 24 hours. The reaction mixture is evaporated in vacuo and the concentrate purified by chromatography on silica gel using 1:2 ethyl acetate-hexanes to 9:1 chloroformmethanol to afford 0.070 g of the desired product. FAB MASS SPEC 596 (M+H).

EXAMPLE 24

2-Butyl-6-[4,5-dihydro-3-(4-methylphenyl)-5-isoxazolyl]-3-[[2'-(lH-tetrazol-5-yl)[1,1'-biphenyl]-4-yl]methyl]-4(3H)-cruinazolinone A mixture of 0.049 g 2-Butyl-6-[4,5-dihydro-3-(4-methylphenyl)-5-isoxazolyl]-3-[[2'-[l-(triphenylmethyl)-lH-tetrazol-5-yl][1,1'-biphenyl-4-yl]methyl]-4(3H)-quinazolinone and 2.0 ml of 3 M HCl in ethyl acetate and 2.0 ml of ether is stirred for 15 minutes at room temperature, diluted with ether and filtered. The cake is dried to afford 0.028 g of the desired product. FAB MASS SPEC 596 (M+H)

EXAMPLE 25

Ethyl 5-[2-butyl-3,4-dihydro-4-oxo-3-[[2'-[1-(triphenylmethyl)-1H-tetrazol-5-yl][1,1'-biphenyl]-4-yl]-methyl]-6-cruinazolinyl]-4,5-dihydro-3-isoxazolecarboxylate A solution of 0.250 g of 2-butyl-6-ethenyl3-[[21-[1-(triphenylmethyl)-1H-tetrazol-5-yl][1,1'-bi-phenyl]-4-yl]methyl]-4(3H)-quinazolinone and 0.054 g of ethyl chlorooximidoacetate in 1.5 ml of tetrahydrofuran is stirred while 0.049 ml of triethylamine in 0.5 ml of tetrahydrofuran is added via a syringe pump over 5 hours, then allowed to stir at room temperature for 18 hours. The reaction mixture is diluted with ethyl acetate and the organic layer washed with water. The organic layer is dried with MGSO filtered and applied to preparative silica gel plates. The plates are eluted with 1:2 ethyl acetate-hexanes to afford 0.153 g of the desired product. FAB MASS SPEC 842 (M+Na).

EXAMPLE 26

Ethyl 5-[2-butyl-3,4-dihydro-4-oxo-3-[[2'-(1H-tetrazol-5-yl)[1,1'-biphenyl]-4-yl]-methyl]-6-cruinazo-linyl]-4,5-dihydro-3-isoxazolecarboxylate A solution of 0.049 g of ethyl 5-[2-butyl-3,4-dihydro-4-oxo-3-[[2'-[1-(triphenylmethyl)-1H-tetrazol-5-yl][1,1'-biphenyl]-4-yl]methyl]-6-quinazolinyl]- 4,5-dihydro-3-isoxazole carboxylate in 2.0 ml of 3 M HCl in ethyl acetate and 2.0 ml of ether is stirred at room temperature for 15 minutes, diluted with ether, filtered and dried to afford 0.072 g of the desired product. FAB MASS SPEC 578 (M+H).

EXAMPLE 27

5-[2-butyl-3.4-dihydro-4-oxo-3-[[2'-[1-(triphenylmethyl)-1H-tetrazol-5-yl][1,1'-biphenyl]-4-yl]-methyl]-6-cruinazolinyl]-4,5-dihydro-3-isoxazolecarboxylic acid A solution of 0.223 g of ethyl 5-[2-butyl-3,4-dihydro-4-oxo-3-[[2'-[1-(triphenylmethyl)-1H-tetrazol-5-yl][1,1'-biphenyl]-4-yl]methyl]-6-quinazolinyl]-4,5-dihydro-3-isoxazole carboxylate in 2.0 ml of 1 N sodium hydroxide and 4.0 ml of (1:1) methanol-tetrahydrofuran is stirred at room temperature for 0.5 hours, acidified with 5% HCl, diluted with brine and extracted with ethyl acetate. The organic layer is dried with MgSO4, filtered and concentrated in vacuo to afford 0.175 g of the desired product. FAB MASS SPEC 814 (M+Na).

EXAMPLE 28

5-[2-butyl-3,4-dihydro-4-oxo-3-[[2'-(1H-tetrazol-5-yl)[1,1'-biphenyl]-4-yl]-methyl]-6-quinazolinyl]-4,5-dihydro-3-isoxazolecarboxylic acid A solution of 0.156 g of S-[2-butyl-3,4-dihydro-4-oxo-3-[[21-[1-(triphenylmethyl)-1H-tetrazol-5-yl][1,1'-biphenyl]-4-yl]methyl]-6-quinazolinyl]-4,5-dihydro-3-isoxazolecarboxylic acid in 2.0 ml of 3 X HCl in ethyl acetate and 2.0 ml of other is stirred at room temperature for 0.5 hour. The reaction mixture is diluted with ether and filtered. The cake is washed with ether-hexanes and the combined filtrates purified on preparative silica gel plates using chloroform-reethanol to afford 0.121 g of the desired product. FAB MASS SPEC 550 (M+H).

Utilizing the methodology described herein the following compound can also be obtained:

Ethyl 5-[2-butyl-3,4-dihydro-4-oxo-3-[[2'-[1-(triphenylmethyl)-1H-tetrazol-5-yl][1,1'-biphenyl]-4-yl]methyl]-6-quinazolinyl]-4,5-dihydro-5-methyl-3-isoxazolecarboxylate.

Angiotensin II Antagonists In Vitro Tests

Materials and Methods

Beef adrenals are obtained from a local slaughter house (Maxwell-Cohen). [$^{125}$I](Sar$^1$,Ile$^8$)AngII, S.A. 2200 Ci/mmole, is purchased from Dupont (KEN@, Boston, Mass.). All unlabeled AngII analogs, Dimethylsulfoxide (DMSO), nucleotides, bovine serum albumin (BBA) are purchased from Sigma Chemical Co., St. Louis, MO U.S.A.

Preparation of Membranes

Approximately sixteen (16) to twenty (20) beef adrenal glands are processed as follows: fresh adrenal glands received on crushed ice are cleaned of fatty tissues and the tough membranes encapsulating the glands are removed and discarded. The brownish tissue forming the adrenal cortex is scraped off and finely minced with scissors before homogenization care is taken to avoid contamination with medullary tissue during dissection. The scraped cortices are suspended in twenty volumes of an ice-cold buffer medium consisting of 10 mM Tris.HCl (pH 7.4 at 220C) and containing 1.0 mM EDTA and 0.2M sucrose. Unless otherwise indicated, all subsequent operations are done at 40C. The tissue is homogenized in a glass homogenizer with a motor-driven teflon pestle with a clearance of 1.0 Mm. The homogenate is centrifuged first at low speed (3,000×g) for 10 min. The resulting pellet is discarded and the supernatant fluid recentrifuged at 10,000×g for 15 minutes to give a P$_2$ pellet. This P$_2$ pellet is discarded and the liquid phase is carefully decanted off in clean centrifuge tubes and recentrifuged at high speed (100,000×g) for 60 min. The translucent final pellet is harvested and combined in a small volume (20–50.0 ml) of 50.0 mN Tris.HCl buffer, pH 7.2. A 100 ul aliquot is withdrawn and the protein content of the preparation is determined by the Lowry's method (Lowry, O. H., Rosebrough, N. P., Parr, A. L. and Randall, R. J., Protein measurement with Folin phenol reagent. J. Biol. Chem., 48, 265–275, 1951). The pelleted membrane is reconstituted in 50.0 mM Tris.HCl buffer containing 0.1 mM of phenylmethylsulfonyl fluoride (PMSF) to give approximately a protein concentration of 2.5 mg per ml of tissue suspension. The membrane preparation is finally aliquoted in 1.0 ml volumes and stored at −70° C. until use in the binding assays.

Receptor Binding Assay

Binding of [$^{125}$I](Sar$^1$,Ile$^8$)AngII

The binding of [$^{125}$I](Sar$^1$,Ile$^8$)AngII to microsomal membranes is initiated by the addition of reconstituted membranes (1:10 vols.) in freshly made 50.0 mM Tris.HCl buffer, pH 7.4 containing 0.25% heat inactivated bovine serum albumin (BSA): 80 ul membrane protein (10 to 20 ug/assay) to wells already containing 100 ul of incubation buffer (as described above) and 20 ul [$^{125}$I](Sar$^1$,Ile$^8$)AngII (Specific Activity, 2200 Ci/mmole). Non-specific binding is measured in the presence of 1.0 uM unlabeled (Sar[1],Ile[8])AngII, added in 20 ul volume. Specific binding for [$^{125}$I](Sar[1],Ile[8]) AngII is greater than 90%. In competition studies, experimental compounds are diluted in dimethylsulfoxide (DMSO) and added in 20 ul to wells before the introduction of tissue membranes. This concentration of DMSO is found to have no negative effects on the binding of [$^{125}$I] (Sar[1],Ile[8]) AngII to the membranes. Assays are performed in triplicate. The wells are left undisturbed for 60 min. at room temperature. Following incubation, all wells are harvested at once with a Brandel ® Harvester especially designed for a 96 well plate (Brandel ® Biomedical Research & Development Labs. Inc., Gaithersburg, MD, U.S.A.). The filter discs are washed with 10×1.0 ml of cold 0.9% NaCl to remove unbound ligand. Presoaking the filter sheet in 0.1% polyethyleneimine in normal saline (PEI/Saline) greatly reduces the radioactivity retained by the filter blanks. This method is routinely used. The filters are removed from the filter grid and counted in a Parkard ® Cobra Gamma Counter for 1 min. (Packard Instrument Co., Downers Grove, Ill, U.S.A.). The binding data are analyzed by the non-linear interactive "LUNDON-11" program (LUNDON SOFTWARE Inc., Cleveland, OH U.S.A.). Compounds that displace 50% of the labelled angiotensin II at the screening dose of 50 μM are considered active compounds and are then evaluated in concentration-response experiments to determine their IC$_{50}$ values. The results are shown in Table I.

TABLE I

| Ex. No. | R$^6$ | X | Angiotensin II Receptor Binding IC$_{50}$ (M) |
|---|---|---|---|
| 19 | CH$_3$-(furan)-C(=N-O-)-CH$_2$-CH(CH$_3$)- | —(CH$_2$)$_3$CH$_3$ | 17.0 × 10$^{-8}$ |
| 21 | CH$_3$-(thiophene)-C(=N-O-)-CH$_2$-CH(CH$_3$)- | —(CH$_2$)$_3$CH$_3$ | 33.0 × 10$^{-8}$ |
| 23 | CH$_3$-(phenyl)-C(=N-O-)-CH$_2$-CH(CH$_3$)- | —(CH$_2$)$_3$CH$_3$ | 7.0 × 10$^{-8}$ |
| 26 | C$_2$H$_5$O$_2$C-C(=N-O-)-CH$_2$-CH(CH$_3$)- | —(CH$_2$)$_3$CH$_3$ | 3.0 × 10$^{-8}$ |
| 28 | HO$_2$C-C(=N-O-)-CH$_2$-CH(CH$_3$)- | —(CH$_2$)$_3$CH$_3$ | 60.0 × 10$^{-8}$ |
| 30 | C$_2$H$_5$O$_2$C-C(=N-O-)-CH$_2$-C(CH$_3$)$_2$- | —(CH$_2$)$_3$CH$_3$ | 20.0 × 10$^{-8}$ |

As can be seen from Table I, the compounds demonstrate excellent Angiotensin II Receptor Binding activity.

The enzyme resin acts on a blood plasma α$_2$-globulin, angiotensinogen, to produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

The compounds of this invention inhibit the action of AII. By administering a compound of this invention to a rat, and then challenging with angiotensin II, a blockage of the vasopressor response is realized. The results of this test on representative compounds of this invention are shown in Table II.

AII Challenge

Conscious Male okamoto-Aoki SHR, 16-20 weeks old, weighing approximately 330 g are purchased from Charles River Labs (Wilmington, MA). Conscious rats are restrained in a supine position with elastic tape. The area at the base of the tail is locally anesthetized by subcutaneous infiltration with 2% procaine. The ventral caudal artery and vein are isolated, and a cannula made of polyethylene (PE) 10-20 tubing (fused together by heat) is passed into the lower abdominal aorta and vena cava, respectively. The cannula is secured, heparinized (1,000 I.U./ml), sealed and the wound is closed. The animals are placed in plastic restraining cages in an upright position. The cannula is attached to a Statham P23Db pressure transducer, and pulsatile blood pressure is recorded to 10-15 minutes with a Gould Brush recorder. (Chan et al., (Drug Development Res., 18:75-94, 1989).

Angiotensin II (human sequence, Sigma Chem. Co., St. Louis, MO) of 0.05 and 0.1 ug/kg i.v. is injected into all rats (predosing response). Then a test compound, vehicle or a known angiotensin II antagonist is administered i.v., i.p. or orally to each set of rats. The two doses of angiotensin II are given to each rat again at 30, 60, 90, 120, 180, 240 and 300 minutes post dosing the compound or vehicle. The vasopressor response of angiotensin II is measured for the increase in systolic blood pressure in mmhg. The percentage of antagonism or blockade of the vasopressor response of angiotensin II by a compound is calculated using the vasopressor response (increase in systolic blood pressure) of angiotensin II of each rat predosing the compound as 100%. A compound is considered active if at 30 mg/kg i.v. it antagonized at least 50% of the response.

| | Dose (mg/kg) | AII Dose mcg/kg IV | Min Post Dose | Control Before AII | Response After AII | Change | Average Change | & Inhibition |
|---|---|---|---|---|---|---|---|---|
| | | ANGIOTENSIN II (AII) VASOPRESSOR RESPONSE | | | | | | |
| CONTROL | | 0.05 | 0 | 175 | 205 | 30 | 30 | |
| | | | | 170 | 200 | 30 | | |
| | | 0.1 | | 175 | 220 | 45 | 45 | |
| | | | | 170 | 215 | 45 | | |
| Ex. No. 19 | 15 I.V. | 0.05 | 30 | 165 | 165 | 0 | 5 | 83 |
| | | | | 150 | 160 | 10 | | |
| | | 0.1 | | 165 | 165 | 0 | 5 | 89 |
| | | | | 160 | 170 | 10 | | |
| | | 0.05 | 60 | 155 | 165 | 10 | 10 | 67 |
| | | | | 150 | 160 | 10 | | |
| | | 0.1 | | 165 | 165 | 0 | 5 | 89 |
| | | | | 160 | 170 | 10 | | |
| | | 0.05 | 90 | 155 | 160 | 5 | 5 | 83 |
| | | | | 150 | 155 | 5 | | |
| | | 0.1 | | 155 | 165 | 10 | 7.5 | 83 |
| | | | | 150 | 155 | 5 | | |
| | | 0.05 | 120 | 150 | 155 | 5 | 7.5 | 75 |
| | | | | 150 | 160 | 10 | | |
| | | 0.1 | | 155 | 165 | 10 | 7.5 | 83 |
| | | | | 155 | 160 | 5 | | |
| | | 0.05 | 180 | 160 | 160 | 0 | 7.5 | 75 |
| | | | | 140 | 155 | 15 | | |
| | | 0.1 | | 170 | 170 | 0 | 10 | 78 |
| | | | | 150 | 170 | 20 | | |
| SPONTANEOUSLY HYPERTENSIVE RATS n = 2 Body weight(s): 275, 280 grams | | | | | | | | |
| CONTROL | | 0.05 | 0 | 165 | 210 | 45 | 56 | |
| | | | | 170 | 237 | 67 | | |
| | | 0.1 | | 165 | 215 | 50 | 65 | |
| | | | | 165 | 245 | 80 | | |
| Ex. No. 19 | 5 I.V. | 0.05 | 30 | 165 | 176 | 11 | 15.5 | 72 |
| | | | | 200 | 180 | 20 | | |
| | | 0.1 | | 160 | 180 | 20 | 17.5 | 83 |
| | | | | 205 | 220 | 15 | | |
| | | 0.05 | 60 | 160 | 180 | 20 | 15 | 73 |
| | | | | 195 | 205 | 10 | | |
| | | 0.1 | | 160 | 185 | 25 | 21 | 68 |
| | | | | 193 | 210 | 17 | | |
| | | 0.05 | 90 | 155 | 180 | 25 | 20 | 64 |
| | | | | 190 | 205 | 15 | | |
| | | 0.1 | | 175 | 200 | 25 | 24 | 63 |
| | | | | 187 | 210 | 23 | | |
| | | 0.05 | 120 | 150 | 185 | 35 | 25 | 55 |
| | | | | 175 | 190 | 15 | | |
| | | 0.1 | | 165 | 185 | 20 | 22.5 | 65 |
| | | | | 175 | 200 | 25 | | |
| | | 0.05 | 180 | 165 | 198 | 33 | 25 | 55 |
| | | | | 185 | 202 | 17 | | |
| | | 0.1 | | 170 | 195 | 25 | 27.5 | 58 |
| | | | | 185 | 215 | 30 | | |
| SPONTANEOUSLY HYPERTENSIVE RATS n = 2 Body weight(s): 300, 260 grams | | | | | | | | |
| CONTROL | | 0.05 | 0 | 170 | 225 | 55 | 47.5 | |

-continued

| | | ANGIOTENSIN II (AII) VASOPRESSOR RESPONSE | | | | | | |
|---|---|---|---|---|---|---|---|---|
| | Dose (mg/kg) | AII Dose mcg/kg IV | Min Post Dose | Control Before AII | Response After AII | Change | Average Change | & Inhibition |
| | | | | 175 | 215 | 40 | | |
| | | 0.1 | | 175 | 224 | 49 | 47 | |
| | | | | 175 | 220 | 45 | | |
| Ex. No. 21 | 5 I.V. | 0.05 | 30 | 188 | 205 | 17 | 13.5 | 72 |
| | | | | 180 | 190 | 10 | | |
| | | 0.1 | | 180 | 210 | 30 | 27.5 | 41 |
| | | | | 175 | 200 | 25 | | |
| | | 0.05 | 60 | 175 | 210 | 35 | 25 | 47 |
| | | | | 175 | 190 | 15 | | |
| | | 0.1 | | 175 | 213 | 38 | 34 | 28 |
| | | | | 165 | 195 | 30 | | |
| | | 0.05 | 90 | 170 | 195 | 25 | 24 | 49 |
| | | | | 157 | 180 | 23 | | |
| | | 0.1 | | 175 | 215 | 40 | 31 | 34 |
| | | | | 163 | 185 | 22 | | |
| | | 0.5 | 120 | 185 | 220 | 35 | 27.5 | 42 |
| | | | | 160 | 180 | 20 | | |
| | | 0.1 | | 175 | 215 | 40 | 31.5 | 33 |
| | | | | 160 | 183 | 23 | | |
| | | 0.05 | 180 | 170 | 210 | 40 | 30 | 37 |
| | | | | 160 | 180 | 20 | | |
| | | 0.1 | | 175 | 225 | 50 | 40 | 15 |
| | | | | 160 | 190 | 30 | | |
| SPONTANEOUSLY HYPERTENSIVE RATS n = 2 Body weight(s): 320, 290 grams | | | | | | | | |
| CONTROL | | 0.05 | 0 | 185 | 230 | 45 | 56 | |
| | | | | 170 | 237 | 67 | | |
| | | 0.1 | | 188 | 230 | 42 | 53.5 | |
| | | | | 170 | 235 | 65 | | |
| Ex. No. 26 | 10 I.V. | 0.05 | 30 | 180 | 195 | 15 | 15 | 73 |
| | | | | 175 | 190 | 15 | | |
| | | 0.1 | | 185 | 192 | 7 | 11 | 79 |
| | | | | 170 | 185 | 15 | | |
| | | 0.05 | 60 | 175 | 195 | 20 | 10.5 | 81 |
| | | | | 195 | 196 | 1 | | |
| | | 0.1 | | 180 | 195 | 15 | 12.5 | 77 |
| | | | | 175 | 185 | 10 | | |
| | | 0.05 | 90 | 175 | 190 | 15 | 17 | 70 |
| | | | | 165 | 184 | 19 | | |
| | | 0.1 | | 185 | 200 | 15 | 15 | 72 |
| | | | | 175 | 190 | 15 | | |
| | | 0.05 | 120 | 165 | 185 | 20 | 20 | 64 |
| | | | | 165 | 185 | 20 | | |
| | | 0.1 | | 175 | 192 | 17 | 18.5 | 65 |
| | | | | 165 | 185 | 20 | | |
| | | 0.05 | 180 | 170 | 185 | 15 | 17.5 | 69 |
| | | | | 165 | 185 | 20 | | |
| | | 0.1 | | 170 | 207 | 37 | 38.5 | 28 |
| | | | | 165 | 205 | 40 | | |
| SPONTANEOUSLY HYPERTENSIVE RATS n = 2 Body weight(s): 310, 300 grams | | | | | | | | |
| CONTROL | | 0.05 | 0 | 205 | 237 | 32 | 40 | |
| | | | | 175 | 223 | 48 | | |
| | | 0.1 | | 195 | 250 | 55 | 52.5 | |
| | | | | 175 | 225 | 50 | | |
| Ex. No. 28 | 15 I.V. | 0.05 | 30 | 185 | 195 | 10 | 10 | 75 |
| | | | | 167 | 177 | 10 | | |
| | | 0.1 | | 190 | 199 | 9 | 4.5 | 91 |
| | | | | 165 | 165 | 0 | | |
| | | 0.05 | 60 | 170 | 175 | 5 | 2.5 | 94 |
| | | | | 165 | 165 | 0 | | |
| | | 0.1 | | 175 | 190 | 15 | 14 | 73 |
| | | | | 157 | 170 | 13 | | |
| | | 0.05 | 90 | 185 | 195 | 10 | 10 | 75 |
| | | | | 185 | 195 | 10 | | |
| | | 0.1 | | 185 | 195 | 10 | 10 | 81 |
| | | | | 175 | 185 | 10 | | |
| | | 0.05 | 120 | 163 | 185 | 22 | 16 | 60 |
| | | | | 165 | 175 | 10 | | |
| | | 0.1 | | 180 | 200 | 20 | 20 | 62 |
| | | | | 165 | 185 | 20 | | |
| | | 0.05 | 180 | 170 | 186 | 16 | 15.5 | 61 |
| | | | | 170 | 185 | 15 | | |
| | | 0.1 | | 175 | 199 | 24 | 24.5 | 53 |
| | | | | 160 | 185 | 25 | | |
| SPONTANEOUSLY HYPERTENSIVE RATS n = 2 Body weight(s): 300, 290 grams | | | | | | | | |
| CONTROL | | 0.05 | 0 | 190 | 217 | 27 | 46 | |
| | | | | 200 | 265 | 65 | | |
| | | 0.1 | | 200 | 230 | 30 | 40 | |
| | | | | 215 | 265 | 50 | | |
| Ex. No. | 15 I.V. | 0.05 | 30 | 175 | 190 | 15 | 10 | 78 |

| Dose (mg/kg) | AII Dose mcg/kg IV | Min Post Dose | Control Before AII | Response After AII | Change | Average Change | & Inhibition |
|---|---|---|---|---|---|---|---|
| 30 | | | 215 | 220 | 5 | | |
| | 0.1 | | 170 | 184 | 14 | 17 | 58 |
| | | | 210 | 230 | 20 | | |
| | 0.05 | 60 | 190 | 190 | 0 | 9 | 80 |
| | | | 207 | 225 | 18 | | |
| | 0.1 | | 185 | 200 | 15 | 20 | 50 |
| | | | 200 | 225 | 25 | | |
| | 0.05 | 90 | 170 | 190 | 20 | 20 | 57 |
| | | | 210 | 230 | 20 | | |
| | 0.1 | | 165 | 200 | 35 | 32.5 | 19 |
| | | | 205 | 235 | 30 | | |
| | 0.05 | 120 | 165 | 205 | 40 | 35 | 24 |
| | | | 200 | 230 | 30 | | |
| | 0.1 | | 175 | 200 | 25 | 29 | 28 |
| | | | 200 | 233 | 33 | | |
| 15 I.V. | 0.05 | 180 | 200 | 205 | 5 | 5 | 89 |
| | | | 240 | 245 | 5 | | |
| | 0.1 | | 190 | 215 | 25 | 15 | 63 |
| | | | 240 | 245 | 5 | | |

SPONTANEOUSLY HYPERTENSIVE RATS n = 2 Body weight(s): 290, 310 grams

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response for example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

What is claimed is:

1. A quinazolinone compound having the formula:

5,284,853

31

Formula I

[Structure: benzamide with substituents R⁵, R⁶, R⁷, R⁸ on aromatic ring, N=X imine, and N-CH₂-biphenyl-R group]

wherein:
R is

[Structure: tetrazole ring with NH]

X is straight or branched alkyl of 3 to 5 carbon atoms;
R⁶ is

[Structure: isoxazoline with R¹, R³, R¹⁴, R¹⁶ substituents, N—O]

R¹ is H, straight chain lower alkyl of 1 to 4 carbon atoms, —CF₃, —CN, $-\overset{O}{\underset{\|}{C}}-OR^9$, $-\overset{O}{\underset{\|}{C}}-NR^9R^9$, phenyl, substituted phenyl (substitution selection from mono-lower alkyl of 1 to 3 carbon atoms, —CP₃, nitro, O-alkyl of 1 to 3 carbon atoms), pyridinyl, thieneyl or furyl
R³ is —CO₂R⁹,

[Structures: furan-R⁹, thiophene-R⁹], —CH₂OR⁹, phenyl, substituted phenyl (substitution selection from mono-lower alkyl of 1 to 3 carbon atoms, —CF₃, nitro, O-alkyl of 1 to 3 carbon atoms), pyridinyl, —CN, alkyl(C₁-C₆) straight or branched, $-\overset{O}{\underset{\|}{C}}-R^9$, $-\overset{O}{\underset{\|}{C}}-NR^{19}R^{19}$;

R¹⁴ and R¹⁶ are hydrogen, straight or branched chain lower alkyl of 1 to 4 carbon atoms, —CO₂R⁹, —CN, phenyl, substituted phenyl (substitution selected from monolower alkyl of 1 to 3 carbon

32 atoms, —CF₃, nitro, O-alkyl of 1 to 3 carbon atoms) pyrdinyl, thienyl, furyl $-\overset{O}{\underset{\|}{C}}-R^9$, or $-\overset{O}{\underset{\|}{C}}-NR^9R^9$;

R¹⁹ is straight or branched chain lower alkyl of 1 to 4 carbon atoms;
R⁹ is hydrogen, straight chain or branched lower alkyl of 1 to 4 carbon atoms; or pharmaceutically acceptable salts thereof.

2. The compound according to claim 1 wherein said salts are selected from potassium, sodium calcium, magnesium or ammonium.

3. The compound according to claim 1 wherein
X is a straight chain alkyl of 3 or 4 carbon atoms;
R⁶ is

[Structure: CH₃-furan-isoxazoline]

[Structure: CH₃-thiophene-isoxazoline]

[Structure: CH₃-phenyl-isoxazoline]

[Structure: C₂H₅O₂C-isoxazoline]

[Structure: HO₂C-isoxazoline]

[Structure: C₂H₅O₂C-isoxazoline with CH₃]

4. A quinazolinone compound having the formula:

[Structure: quinazolinone with R⁶, X, N-CH₂-biphenyl-R¹⁸]

wherein:

X is straight or branched alkyl of 3 to 5 carbon atoms;
R$^{18}$ is

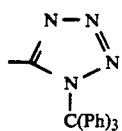

R$^6$ is

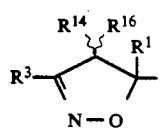

R$^1$ is H, straight chain lower alkyl of 1 to 4 carbon atoms, —CF$_3$, —CN,

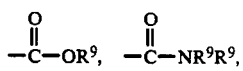

phenyl, substituted phenyl (substitution selection from mono-lower alkyl of 1 to 3 carbon atoms, —CF$_3$, nitro, O-alkyl of 1 to 3 carbon atoms), pyridinyl, thienyl or furyl;
R$^3$ is —CO$_2$R$^9$,

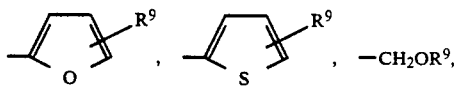

phenyl, substituted phenyl (substitution selection from mono-lower alkyl of 1 to 3 carbon atoms, —CF$_3$, nitro, O-alkyl of 1 to 3 carbon atoms), pyridinyl, —CN, alkyl(C$_1$-C$_6$) straight or branched,

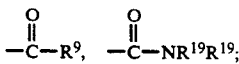

R$^{14}$ and R$^{16}$ are hydrogen, straight or branched lower alkyl of 1 to 4 carbon atoms, —CO$_2$R$^9$, —CN, phenyl, substituted phenyl (substitution selected from mono-lower alkyl of 1 to 3 carbon atoms, —CF$_3$, nitro, O-alkyl of 1 to 3 carbon atoms, NH$_2$), pyridinyl, thienyl, furyl

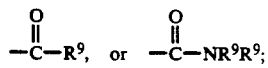

R$^{19}$ is straight or branched chain lower alkyl of 1 to 4 carbon atoms;
R$^9$ is hydrogen, straight chain lower alkyl of 1 to 4 carbon atoms.

5. The compound according to claim 4 wherein X is a straight chain alkyl of 3 or 4 carbon atoms;
R$^6$ is

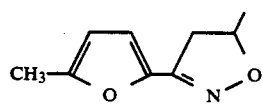

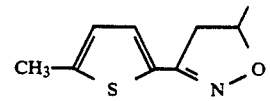

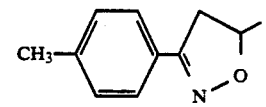

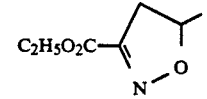

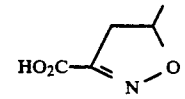

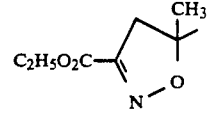

6. The compound according to claim 1 2-Butyl-6-[4,5-dihydro-3-(5-methyl-2-furanyl)-5-isoxazolyl]-3-[[21-(lH-tetrazol-5-yl)[1,1'-biphenyl]-4-yl]methyl]-4(3H)-quinazolinone.

7. The compound according to claim 1 2-Butyl-6-[4,5-dihydro-3-(5-methyl-2-thienyl)-5-isoxazolyl]-3-[[21-(lH-tetrazol-5-yl)[1,1'-biphenyl]-4-yl]methyl]-4(3H)-quinazolinone.

8. The compound according to claim 1 2-Butyl-6-[4,5-dihydro-3-(4-methylphenyl)-5-isoxazolyl]-3-[[21-(lH-tetrazol-5-yl)[1,11-biphenyl]-4-yl]methyl]-4(3H)-quinazolinone.

9. The compound according to claim 1 ethyl 5-[2-butyl-3,4-dihydro-4-oxo-3[[2'-(lH-tetrazol-5-yl)[1,1'-biphenyl]-4-yl]-methyl]-6-quinazolinyl]-4,5-dihydro-3-Isoxazolecarboxylate.

10. The compound according to claim 1 5-[2-butyl-3,4-dihydro-4-oxo-3-[[2'-(lH-tetrazol-5-yl)-[1,1'-biphenyl]-4-yl]-methyl]-6-quinazolinyl]-4,5-dihydro-3-isoxazolecarboxylic acid.

11. The compound according to claim 1 ethyl 5-[2-butyl-3,4-dihydro-4-oxo-3-[[2'-(lH-tetrazol-5-yl)[1,1'-biphenyl]-4-yl]-methyl]-6-quinazolinyl]-4,5-dihydro-5-methyl-3-isoxazolecarboxylate.

12. The compound according to claim 4 4'-[[2-butyl-6-[4,5-dihydro-3-(5-methyl-2-furanyl)-5-isoxazolyl]-4-oxo-3(4H)-quinazolinyl]methyl][1,1'-biphenyl]-2-carbonitrile.

13. The compound according to claim 4 4'-[[2-butyl-6-[4,5-dihydro-3-(5-methyl-2-thienyl)-5-isoxazolyl]-4-oxo-3(4H)-quinazolinyl]methyl][1,1'-biphenyl]-2-carbonitrile.

14. The compound according to claim 4 2-Butyl-6-[4,5-dihydro-3-(4-methylphenyl)-5-isoxazolyl]-3-[[21-[1-(triphenylmethyl)-lH-tetrazol-5-yl][1,1'-biphenyl-4-yl]methyl]-4(3H)-quinazolinone.

15. The compound according to claim 4 Ethyl 5-[2-butyl-3,4-dihydro-4-oxo-3-[[2'-[l-(triphenylmethyl)-lH-tetrazol-5-yl][1,1'-biphenyl]-4-yl]-methyl]-6-quinazolinyl]-4,5-dihydro-3-isoxazolecarboxylate.

16. The compound according to claim 4 5-[2-butyl-3,4-dihydro-4-oxo-3-[[2'-[1-(triphenylmethyl)-1H-tetrazol-5-yl]-[1,11-biphenyl]-4-yl]-methyl]-6-quinazolinyl]-4,5-dihydro-3-isoxazolecarboxylic acid.

17. The compound according to claim 4 Ethyl 5-[2-butyl-3,4-dihydro-4-oxo-3-[[2'-[l-(triphenylmethyl)-1H-tetrazol-5-yl][1,1'-biphenyl]-4-yl]-methyl]-6-quinazolinyl]-4,5-dihydro-5-methyl-3-isoxazolecarboxylate.

18. A pharmaceutical composition useful for treating angiotensin induced hypertension or congestive heart failure in a mammal comprising a suitable pharmaceutical carrier and an effective amount of a compound of claim 1.

19. A method of treating angiotensin induced hypertension in a mammal comprising administering a compound of claim 1 to said mammal an amount effective to lower angiotensin induced hypertension.

20. A method of treating congestive heart failure in a mammal comprising administering a compound of claim 1 to said mammal in an amount effective to treat congestive heart failure.

21. A method of antagonizing the effects of Angiotensin II in a mammal comprising administering a compound of claim 1 to said mammal in an amount effective to treat the effects of Angiotensin II.

* * * * *